(12) United States Patent
Strait et al.

(10) Patent No.: US 12,161,713 B2
(45) Date of Patent: Dec. 10, 2024

(54) PRIME-BOOST VACCINATION REGIMEN

(71) Applicant: Intervet Inc., Madison, NJ (US)

(72) Inventors: Erin Linn Strait, Spring Hill, KS (US); Mark A. Mogler, Ames, IA (US); Pravina Kitikoon, Overland Park, KS (US); Ruud Philip Antoon Maria Segers, Boxmeer (NL); Erwin van den Born, Wageningen (NL)

(73) Assignee: Intervet Inc., Rahway, NJ (US)

(*) Notice: Subject to any disclaimer, the term of this patent is extended or adjusted under 35 U.S.C. 154(b) by 630 days.

(21) Appl. No.: 17/414,187

(22) PCT Filed: Dec. 19, 2019

(86) PCT No.: PCT/EP2019/086305
§ 371 (c)(1),
(2) Date: Jun. 15, 2021

(87) PCT Pub. No.: WO2020/127730
PCT Pub. Date: Jun. 25, 2020

(65) Prior Publication Data
US 2022/0023414 A1    Jan. 27, 2022

Related U.S. Application Data (60) Provisional application No. 62/782,508, filed on Dec. 20, 2018.

(51) Int. Cl.
| | | |
|---|---|---|
| *A61K 39/215* | (2006.01) | |
| *A61K 39/12* | (2006.01) | |
| *A61P 31/14* | (2006.01) | |
| *C12N 7/00* | (2006.01) | |
| *A61K 39/00* | (2006.01) | |

(52) U.S. Cl.
CPC ............ *A61K 39/215* (2013.01); *A61K 39/12* (2013.01); *A61P 31/14* (2018.01); *C12N 7/00* (2013.01); *A61K 2039/5254* (2013.01); *A61K 2039/5258* (2013.01); *A61K 2039/545* (2013.01); *A61K 2039/552* (2013.01); *C12N 2770/10023* (2013.01); *C12N 2770/10034* (2013.01); *C12N 2770/10071* (2013.01); *C12N 2770/20034* (2013.01); *C12N 2770/20071* (2013.01)

(58) Field of Classification Search
None
See application file for complete search history.

(56) References Cited

U.S. PATENT DOCUMENTS

| | | |
|---|---|---|
| 7,927,858 B2 | 4/2011 | Mayeresse |
| 8,021,670 B2 | 9/2011 | Drexler et al. |
| 2003/0068360 A1* | 4/2003 | Audonnet ............ A61K 47/24 514/642 |
| 2018/0008699 A1* | 1/2018 | Chang .................. A61K 39/12 |

FOREIGN PATENT DOCUMENTS

| | | |
|---|---|---|
| RU | 2333770 C2 | 9/2008 |
| RU | 2408386 C2 | 1/2011 |
| RU | 2015132962 | 2/2017 |
| WO | 2005046621 A2 | 5/2005 |
| WO | 2008127307 A2 | 10/2008 |
| WO | 2011028652 | 3/2011 |
| WO | 2014108515 | 7/2014 |
| WO | 2017088060 | 6/2017 |

OTHER PUBLICATIONS

Hikke, M et al, Veterinary Replicon Vaccines, Annu. Rev. Anim. Biosci., Nov. 3, 2016, pp. 10.1-10.21, 5.
International Search Report and Written Opinion for PCT/EP2019/086305, mailed Apr. 29, 2020; 15 pages.
Murgia, Maria V. et al., Evaluation of an African swine fever (ASF) vaccine strategy incorporating priming with an alphavirus-expressed antigen followed by boosting with attenuated ASF virus, Archives of Virology, 2018, 359-370, 164(2).
Cherenova L.V., et al., Development of Vaccines Based on Adenoviral Vectors: a Review of Foreign Clinical Studies (Part 2), Medical Immunology (Russia), 19(4), 329-358, 2017.
I.V. Dolzhikova, et al., Virus-Vectored Ebola Vaccines, Acta Naturae, vol. 9 No. 3 (34), 4-11, 2017.
Kardani, Kimia et al., Prime-boost vaccine strategy against viral infections: Mechanisms and benefits, Vaccine, 34 413-423, 2016.
Lu, Shan, Heterologous prime-boost vaccination, Current Opinion in Immunology, 21, 346-351, 2009.
Petrov, A. A. et al., Future Developments and Applications of the Vaccines against Dangerous Viral Infections, RNA-Replicon-Based, Obtained from the Venezuelan Equine Encephalomyelitis Virus, The 48th Central Research Institute the Minis fly of Defense, Sergiev Possad, Russian Federation, 3, 86-91, 2014.

(Continued)

*Primary Examiner* — Shanon A. Foley
(74) *Attorney, Agent, or Firm* — Susanna C. Benn; Jenny Cromsigt (57) ABSTRACT

The present invention relates to a method of vaccination. Specifically the invention regards to a prime-boost vaccination regimen for protecting a target animal against infection or disease caused by a virus, wherein the vaccination regimen comprises the administration to said target animal of a vaccine comprising a live attenuated form of said virus, followed by the administration to said target animal of a vaccine comprising an RP encoding one or more antigens from said virus.

6 Claims, 2 Drawing Sheets

(56) References Cited

OTHER PUBLICATIONS

Petrov, A. A. et al., Future Developments and Applications of the Vaccines against Dangerous Viral Infections, RNA-Replicon-Based, Obtained from the Venezuelan Equine Encephalomyelitis Virus, The 48th Central Research Institute of the Ministry of Defense, Sergiev Possad, Russian Federation, 3, 86-91, 2014.

Ushakov, D.N., Ushakov's Explanatory Dictionary, Ushakov's Explanatory Dictionary, N/A, 2 pages, https://dic.academic.ru/dic.nsf/ushakov/1048530, 1935-1940.

Yarilin, A.A., Fundamentals of Immunology, Moscow "Medicine", N/A, 405, 1999.

* cited by examiner

PRIME-BOOST VACCINATION REGIMEN

CROSS-REFERENCE TO RELATED APPLICATIONS

This application is a National Stage application of International Patent Application No. PCT/EP2019/086305, filed Dec. 19, 2019, which claims priority to U.S. Provisional Patent Application No. 62/782,508, filed Dec. 20, 2018.

The present invention relates to the field of vaccination; more specifically the invention relates to a method of vaccination for protecting a target animal against infection or disease caused by a virus.

Infections by pathogenic viruses and their resulting diseases are known since the beginning of civilization, affecting both humans and animals with often serious effects on health and well-being. Since the 1800's virus infections have been countered by active immunization. Such vaccination comprises the administration to a target animal of an attenuated- or killed form of the viral pathogen. An attenuated virus vaccine (a.k.a. a modified live vaccine) comprises a replicating but relatively harmless virus, which by its replication in the target animal induces a protective immune response against the corresponding pathogenic form of the virus.

Because most viruses are relatively simple structures, the use of a single antigen from their antigen profile can sometimes suffice to generate a protective immune response. Such a subunit vaccine can be manufactured by extraction from the virus or its culture, or by the recombinant expression of the specific antigen. Alternatively, the viral antigen can be delivered to a target animal and expressed inside it, by a live recombinant carrier micro-organism that acts as a vector. Examples of viral vectors are Adenovirus for use in humans, and Herpes virus of turkeys for chickens.

A variation on the use of viral vector vaccines is the use of vaccines of replicon particles (RP; see Lundstrom, 2014, Vaccines, vol. 6, p. 2392-2415). These are virus-like particles but comprise a defective viral genome and typically, a heterologous gene. These replicon particles comprise RNA packaged in particles (i.e., they are encapsidated) such that they are able to enter a target animal host cell and perform one round of viral genome amplification without the ability to form new particles. The replicon particle does not propagate from the infected cell, as it lacks the necessary structural protein-coding sequence(s)). As such, they are more similar to wild-type virus than other replicon vaccines such as naked RNA vaccines, or vaccines comprising RNA launched from a DNA plasmid (Hikke, 2017, Anu. Rev. Anim. Biosci. 2017, 5; 10.1-10.21). The genome of the RP's typically express a heterologous gene encoding an immunoprotective antigen. Multiple RNA viruses have been used in the production of RP's, such as members of the positive stranded Flaviviridae, Picornaviridae and Arteriviridae, or negative stranded RNA viruses such as Bunyavirus, Paramyxovirus and Rhabdovirus. Most widely used and most extensively studied are Alphavirus RNA replicon particles (Vander Veen et al., 2012, Anim. Health. Res. Rev., vol. 13, p. 1-9; and: Kamrud et al., 2010, J. Gen. Virol., vol. 91, p. 1723-1727), which are therefore preferred for practical reasons. Also, Alphavirus RP's are believed to be somewhat stronger immunopotentiators than other RP's known in the art and based on other viruses such as the bunyavirus. Several Alphavirus species have been used to develop RP vaccines, e.g.: Venezuelan equine encephalitis virus (VEEV) (Pushko et al., 1997, Virology, vol. 239, p. 389-401), Sindbis virus (Bredenbeek et al., 1993, J. of Virol., vol. 67, p. 6439-6446), and Semliki Forest virus (Liljestrom & Garoff, 1991, Biotechnology (NY), vol. 9, p. 1356-1361).

RP vaccines can elicit mucosal and systemic immune responses following immunization of a target animal (Davis et al., 2002, IUBMB Life, vol. 53, p. 209-211). RP vaccines (VEE based) are also the basis of several USDA-licensed vaccines, which include: Porcine Epidemic Diarrhea Vaccine, RNA (Product Code 19U5.P1), Swine Influenza Vaccine, RNA (Product Code 19A5.D0), Avian Influenza Vaccine, RNA (Product Code 1905.D0), and Prescription Product, RNA Particle (Product Code 9PP0.00). Also: Wang et al., 2018, Vaccine, vol. 36, p. 683-690.

For inactivated- and subunit vaccines the use of an immuno-stimulant for optimal efficacy is common. As an excipient, such an adjuvant needs to be pharmaceutically acceptable, and cost effective. Well known adjuvants are aluminum salts and oils. Oil adjuvants can be of mineral- or non-mineral origin, whereby mineral oils are generally only allowed for veterinary use.

In veterinary practice, vaccinations are routinely administered to live-stock- or companion animals. In the live-stock sector, economy of operation is an important concern as it is typically a high volume-low margin operation. Consequently, vaccinations for animal husbandry need to be effective and affordable. Efficacy is thereby regarded in respect of the number of vaccinations that need to be given to achieve strong immune protection, and the breadth of the protection obtained. This last aspect is especially relevant for viral vaccines as viruses can quickly mutate and emerge as a new variant. A result is that established viral vaccine products may lose efficacy over time.

The optimization of viral vaccination in terms of efficacy and breadth of protection is therefore a constant concern in the field of animal vaccination.

A well-known practice to improve vaccination efficacy is to administer a vaccine more than once. In case of such repeated vaccination the first administration is typically called: the priming vaccination, and the subsequent vaccination(s): the booster vaccination(s). In such a prime-boost vaccination regimen, the two or more administrations can be done using the same vaccine product, in which case the regimen is called a homologous prime-booster regimen. For example, two or more administrations of a vaccine comprising a live attenuated form of a virus, or of a vaccine comprising an inactivated virus. Alternatively, the vaccinations can be done using different vaccine products intended to protect against the same pathogen or disease. In that case this is a heterologous prime-boost vaccination regimen. A review is: Kardani et al., 2016 (Vaccine, vol. 34, p. 413-423), which describes that the majority of heterologous prime-boost vaccination regimens apply a combination of priming vaccination with a vaccine comprising a live attenuated form of a virus, followed some time later by one or more boosters with a vaccine comprising an inactivated virus.

Porcine epidemic diarrhea virus (PEDV), a Coronavirus, was first observed among English feeder and fattening pigs in 1971; these are 'classic' strains like CV777. Later, outbreaks of highly virulent PEDV strains emerged in Asia in 2010 causing high mortality, and currently PEDV is one of the main pathogens giving large economic losses in the swine industry in Asia. An Asian-like PEDV strain was detected in the United States of America in April 2013 and has spread to Canada and South America.

In pigs, severity of disease is variable and dependent on the epidemiologic status of the herd. Particularly suckling pigs are very susceptible, and they typically display watery diarrhea, dehydration, and metabolic acidosis with high mortality. On the other hand, feeder and grower pigs display diarrhea, anorexia, and depression with high morbidity, but low mortality.

Vaccines against PEDV have been described, also for application in heterologous prime-boost vaccination regimens of live+inactivated vaccination, see WO 2016/007576, and WO 2016/007955. However, a homologous prime-boost regimen of 2× inactivated PEDV vaccine was described as highly effective: Paudel et al., 2014 (Vet. Quart., vol. 34, p. 194-200).

Porcine reproductive and respiratory syndrome virus (PRRSV), an Arterivirus, was first reported in 1987, and in the early 1990's had become pandemic. The virus causes significant losses in the swine industry due to reproductive disorders and growth retardation. PRRSV plays a significant role in the generation of multifactorial swine respiratory disease. Clinical symptoms are abortions and stillborn or mummified fetuses, and cyanosis of the ear and vulva. In neonatal and weaned pigs, the virus causes respiratory distress, with increased susceptibility to secondary respiratory infections. However subclinical infections are also common. The virus is also quite variable: there are two distinct variants of the species described: genotype 1 (formerly known as European) and genotype 2 (formerly known as North American), and the strain divergence within these two genotypes is large.

Vaccines against PRRSV based on inactivated virus have been described and are commercially available. However, vaccines based on live attenuated virus are considered more effective. Examples are: Porcilis™ PRRS (MSD Animal Health), Ingelvac PRRS™ MLV (Boehringer Ingelheim), and Fostera™ PRRS (Zoetis).

It is an object of the present invention to overcome a disadvantage in the prior art, and to accommodate to a need in the field by providing a vaccination regimen that can improve the immune protection of a vaccine against infection or disease caused by a viral pathogen.

Surprisingly it was found that this object can be met, and consequently one or more disadvantages of the prior art can be overcome, by applying a heterologous prime-boost vaccination regimen employing a vaccine comprising a live attenuated form of a virus and a vaccine comprising an RP encoding a heterologous viral antigen. When these two vaccines were administered to a target animal in a specific order, the resulting immune response in the target animal was found to have an improved strength and/or breadth, relative to the response from either of the individual vaccines.

Remarkably, this improvement was not observed when these vaccines were given in reversed order, or even when either of the two vaccines was given repeatedly in a homologous prime-boost regimen.

It is not known exactly how or why this selection of vaccine types, and their administration in this combined regimen, and in this specific order, can cause this improvement. Although the inventors do not want to be bound by any theory or model that might explain these findings, they speculate that the observed improvement in the form of an increased height and/or breadth of the immune response may result from the fact that the prime vaccination with the live attenuated virus is able to start a full or at least elaborate suite of immune responses, including for example an innate immune response, and that the boost vaccination with RP's is therefore better responded to (the immune system being adequately primed), even enabling vaccination based on those genes that are disabled in the live vaccine for making this vaccination safe. Priming with an RP vaccine often gives only a moderate immune response due to the less infective/less immunopotentiating nature of the RP's. The current scheme thus provides the advantage of adequately initiating a good immune response with a relatively safe (but maybe not so efficacious) live vaccine, while enabling a good immune response against those genes (i.e. the corresponding proteins) that are absent in the live vaccine for safety reasons and/or any other genes. This means that the current scheme is believed to be particularly advantageous for those pathogens which appear to need a live vaccine for sufficient stimulation of the immune system, but which by using a (safe) live vaccine on itself (either as a one shot, or multi shot vaccine) does not lead to the best possible degree of protection against that pathogen. Examples of such pathogens may be for example the swine pathogens PRRSv, PEDV, ASF (African Swine Fever).

The discovery of this improvement to the immune response can be put to advantageous use in several ways: it can e.g. increase the strength or the onset of the immune response from a vaccination with a vaccine comprising a live attenuated form of a virus. Alternatively, it can increase the breadth of the immune response of a vaccine comprising an RP, such as for example an Alphavirus RNA based replicon particle. For both this applies even in relation to repeated administrations of either of the single vaccines.

Also, it can be applied to broaden the immune response from a vaccination with either a vaccine comprising a live attenuated form of a virus, or with an vaccine comprising an RP, by administering as the booster vaccination an RP that is encoding one or more antigens from a variant of the virus species used in the priming vaccination. Also, more than one type of RP can be used in the booster vaccination. This can help to provide a broader scope of immune-protection, also against variants of the virus. Further this can help to retain protection from a licensed vaccine comprising a live attenuated virus, even when the pathogenic virus currently in the field has undergone mutations that would otherwise cause it to escape the immune response from the vaccine comprising a live attenuated virus.

A further advantage is that RP vaccines can be generated fairly quickly, which adds flexibility to the design of methods of vaccination according to the invention.

All these are advantageous uses of great benefit to the field of vaccination, made possible by the present invention.

This was not at all obvious from any disclosure in the prior art, as vaccine comprising RPs have only been described fairly recently, no heterologous prime-boost vaccination regimens employing a vaccination scheme as currently claimed have yet been disclosed. Consequently, there was no indication to expect that such an improvement of immune response could occur from applying the method of vaccination according to the invention. So, the inventors had no suggestion to select these particular vaccine types; or to apply these vaccine types in a prime-boost vaccination regimen; or to apply these vaccine types in such a vaccination regimen in this specific order.

Therefore, in one aspect the invention relates to a method of vaccination for protecting a target animal against infection or disease caused by a virus, wherein the method comprises

- the administration to said target animal of a vaccine comprising a live attenuated form of said virus, followed by the administration to said target animal of a vaccine comprising a replicon particle (RP) encoding one or more antigens from said virus.

A "method of vaccination" refers to a procedure with scheduled vaccinations, such as a prime-boost vaccination regimen, against a particular pathogen, here: a virus of a certain species.

Consequently, the terms "prime" and "boost", also known as 'priming' and 'booster' or 'boosting', may be used to refer to the vaccinations applied in the method of vaccination according to the invention, wherein the prime, or priming is the earlier vaccination of a target animal against that virus, and the boost, booster, or boosting is the vaccination against that virus that is applied subsequently. Either of the priming and the booster vaccinations can be given one or more times.

The vaccinations of the method of vaccination according to the invention are separated in time by a period that suffices for the target animal's immune system to initiate a response to the priming vaccination. This period can vary much, e.g. from about 1 week up to many years. This is determined by the characteristics of the virus and/or its disease that is being vaccinated against. Also, this interval depends on the characteristics of the target animal, such as the target animal's life expectancy. The "target animal" for the invention is a human- or a non-human animal. The target animal may require or benefit from the vaccination against infection or disease caused by the virus that the method of vaccination intends to protect against.

The age, weight, sex, immunological status, and other parameters of the target animal to be vaccinated are not critical, although it is clearly favorable to vaccinate healthy target animals, and to vaccinate as early in life as possible.

Via the method of vaccination according to the invention target animals can be protected at one or more different stages of their lifecycle, for example as a suckling-newborn via protective colostrum, as an infant in the first periods of life, as a growing animal being raised or fattened for slaughter, as a pregnant mother which can then provide colostrum to suckling offspring, as an elderly target animal with receding strength of immune system, etc.

The term "comprises" (as well as variations such as "comprise", "comprising", and "comprised") as used herein, refer(s) to all elements, and in any possible combination conceivable for the invention, that are covered by or included in the text section, paragraph, claim, etc., in which this term is used, even if such elements or combinations are not explicitly recited; and does not refer to the exclusion of any of such element(s) or combinations. Consequently, any such text section, paragraph, claim, etc., can also relate to one or more embodiment(s) wherein the term "comprises" (or its variations) is replaced by terms such as "consist of", "consisting of", or "consist essentially of".

The "administration" of the vaccines of the method of vaccination according to the invention to a target animal can be performed using any feasible method and route. Typically, the optimal way of administration will be determined by the type of the vaccine applied, and the characteristics of the target animal and the viral disease that it is intended to protect against. For example: because the vaccine comprising a live attenuated virus comprises a replicative antigen, it can be administered using a method of mass application such as via a drinking water- or spray application. Alternatively, for both the vaccine comprising the live attenuated form of a virus, and the vaccine comprising the RP several routes of parenteral, mucosal, topical or enteral administration are feasible. All this is well known in the art, see e.g. "Veterinary vaccinology" (P. Pastoret et al. ed., 1997, Elsevier, Amsterdam, ISBN 0444819681).

A "vaccine" is a well-known composition which has a medical effect and comprises an immunologically active component and a pharmaceutically acceptable carrier. The carrier can be a liquid or a (particulate) solid. The 'immunologically active component' for the invention in the respective vaccines, are the virus in live attenuated form, or the RP encoding the viral antigen. The vaccines stimulate the immune system of the target animal, and induces an immunological response. The response may originate from the target animal's innate- and/or from the acquired immune system, and may be of the cellular- and/or of the humoral type.

The vaccines in the method of vaccination according to the invention provide "protection", or are "protecting", "against infection or disease" by reducing in a vaccinated target animal the severity of a subsequent infection by the virus for the invention. For example by reducing the number or the duration of the viral replication in the target animal, or shortening or reducing the number, the intensity, or the severity of lesions caused by an infection. Also, or consequentially, the method of vaccination is effective in reducing or ameliorating the (clinical) symptoms of disease that may be caused by such infection or replication, or by the target animal's response to that infection or replication. Similarly, the method of vaccination provides protection to offspring of vaccinated target animals, by the passive immunization provided by maternally derived antibodies, such as from consuming colostrum, or from resorbing egg yolk.

A vaccine's efficacy can be determined e.g. by monitoring the immunological response following vaccination and challenge infection, e.g. by monitoring the target animal's signs of disease, clinical scores, or by re-isolation of the viral pathogen, and comparing these results to a vaccination-challenge response seen in mock-vaccinated target animals.

For the vaccines in the method of vaccination according to the invention the dose or amount of the immunologically active component can be determined in well-known ways, for example: the live attenuated virus or the RP can be titrated, e.g. in animals, in fertilized eggs, or on suitable host cells in culture. The result is then expressed e.g. as plaque forming units (pfu), TCID50 or EID50 per milliliter of the vaccine, or in number of RP/ml. Alternatively the antigen can be quantified by a serologic- or bio-chemical test such as an ELISA or an AlphaLisa™, and expressed in relative units, compared to an appropriate reference standard. All these are well known in the art.

The method of vaccination according to the invention can be used as a prophylactic-, metaphylactic-, or therapeutic treatment.

The "virus" for the invention refers to a certain virus species for the invention. Commonly, viral species are determined and taxonomically characterized by referral to a combination of phenotypic characteristics, such as morphology, nucleic acid type, mode of replication, host organisms, as well as by the type of disease the virus may cause.

The vaccine comprising a live attenuated form of a virus, and the vaccine comprising an RP used in the method of vaccination according to the invention, both relate to the virus for the invention in that the live vaccine comprises an attenuated form of that virus species, and the RP encodes at least one antigenic protein from that virus species.

As the skilled person will appreciate, the taxonomic names used herein, such as the species name of a virus, refer to a taxonomic group in which a micro-organism is currently assigned. However, that taxonomic classification could change in time as new insights can lead to reclassification into a new or different taxonomic group. However, as this does not change the micro-organism itself, or its antigenic repertoire, but only its scientific name or classification, such re-classified micro-organisms remain within the scope of the invention.

The reference to a virus species for the invention includes any virus within that species, including any virus that is a variant within that virus species, for example in respect of a variation in serotype, biotype, pathotype, or genotype within that species. Information on viruses and diseases are for example available from handbooks such as Fields Virology, 6$^{th}$ ed., ISBN: 9781451105636, and "The Merck veterinary manual", 10th ed., 2010, C. M. Kahn edt., ISBN: 091191093X.

A live attenuated form of a certain virus species can be obtained in several ways: for many human- or animal viral diseases vaccines of a live attenuated form of such virus are already available. Examples of licensed vaccines of a live attenuated form of a virus are too numerous to mention, both in the human medical- and in the veterinary field. These can be applied in the method of vaccination according to the invention. The skilled person is more than capable of assessing if and how a vaccine comprising a live attenuated form of a virus can be incorporated in the method of vaccination according to the invention, and make any routine modifications or optimizations if appropriate. See P. Pastoret et al., supra.

Alternatively, a pathogenic- or attenuated form of a virus of a certain virus species may be obtained from a variety of sources, e.g. as field isolate from an organism in the wild or on a farm, or from various laboratories, (depository) institutions, or (veterinary) universities. If no attenuated form of a virus is available, a pathogenic form of that virus can be subjected to methods for its attenuation, such as by passaging in vivo or in vitro, or by in vitro techniques such as chemical- or physical mutagenesis, or by using recombinant DNA technology. The level of attenuation can then be assessed in vitro and in vivo. All this is well known in the field.

An "Alphavirus RNA replicon particle (RP)" is well known as a single-cycle infectious Alphaviral structure, that is replication defective due to the absence of the structural protein genes in its genome. The genome can encode a heterologous gene from its 26S subgenomic promoter. The RP can perform a single round of replication, and in this way deliver and express a heterologous antigen to the immune system of a target animal.

For the invention, the gene that the RP is encoding is a gene that is typically heterologous (i.e. not native) relative to the species of the parental virus from which the replicon structure was derived.

An RP encoding a heterologous viral gene of a certain virus species may already be available, such as the commercially available Alphavirus RNA RP vaccines. Alternatively, it can be generated using well known techniques by incorporating the heterologous nucleic acid encoding an immuno-protective antigen into a viral replicon backbone such as e.g. from a TC-83 VEE Alphavirus. The viral antigen gene(s) can then be expressed from the (26S-Alphavirus) subgenomic promoter, and transcribed replicon RNA can be packaged into RPs by expression of the structural proteins by a packaging cell lines, or via cotransfection into suitable host cells of the replicon RNA and of one or more 'helper' RNA's encoding the structural proteins. The generation of VEE TC-83 RNA replicon particles is for example described in U.S. Pat. Nos. 9,441,247 and 8,460,913. General molecular biological techniques involving cloning, transfection, recombination, selection, and amplification are for example explained in great detail in standard text-books like Sambrook & Russell: "Molecular cloning: a laboratory manual" (2001, Cold Spring Harbour Laboratory Press; ISBN: 0879695773); Ausubel et al., in: Current Protocols in Molecular Biology (J. Wiley and Sons Inc., NY, 2003, ISBN: 047150338X); C. Dieffenbach & G. Dveksler: "PCR primers: a laboratory manual" (CSHL Press, ISBN 0879696540); and "PCR protocols", by: J. Bartlett and D. Stirling (Humana press, ISBN: 0896036421).

A vaccine comprising the RP can be an existing vaccine against the selected virus species. Alternatively, such an RP vaccine can be developed from an existing or newly made RP, using well-known techniques.

The RP for the invention is "encoding one or more antigens from" the virus species for the invention. This can be achieved in different ways. For example, such an RP can encode a polycistronic reading frame, or can encode separate genes, e.g. by using one or more additional copy of the subgenomic promoter to allow expression of separate further protein(s).

Alternatively, or additionally, the vaccine comprising the RP for the invention can comprise more than one type of RP, e.g. each encoding one or more heterologous antigens.

The heterologous antigen(s) encoded by the RP for the invention are "from" the virus species for the invention, whereby the term 'from' serves to indicate that the nucleic acid encoding said antigen originated from a virus from that species. The nucleic acid may have been obtained from a virus sample or a part thereof, or may have been synthesized based on sequence information from that virus. Subsequently, the encoding nucleic acid sequence may have been genetically manipulated to result in a modification, truncation, and/or extension of the amino acid sequence of the expressed protein antigen.

Details of embodiments and of further aspects of the invention will be described below.

The method of vaccination according to the invention is especially useful in veterinary practice because of the relatively low cost-price of its components, its ease of use, and the increased and/or broad immune response it can induce.

Therefore, in an embodiment of the method of vaccination according to the invention the target animal is a (non-human) animal of veterinary relevance. Preferably the animal of veterinary relevance is an animal selected from a bovine, porcine, caprine, ovine, cervine, canine, feline, equine, and avian. More preferably the animal is selected from a bovine, porcine, ovine, canine, feline, equine, and avian. Even more preferably the animal is selected from a porcine, canine, feline, and avian. Still even more preferably the animal is selected from a porcine and avian. Most preferred the animal is a porcine.

In an embodiment of the method of vaccination according to the invention the virus is a virus of relevance to veterinary practice. Preferably the virus is an animal pathogen. More preferably the virus is a pathogen of an animal selected from a bovine, porcine, caprine, ovine, cervine, canine, feline, equine, and avian. More preferably the virus is a pathogen of an animal selected from a bovine, porcine, ovine, canine, feline, equine, and avian. Even more preferably the virus is a pathogen of an animal selected from a porcine, canine, feline, and avian. Still even more preferably the virus is a pathogen of an animal selected from a porcine and avian. Most preferred the virus is a pathogen of a porcine.

For the invention a "porcine" refers to animals of the family of Suidae, and preferably to animals of the genus *Sus*, for example: a wild or a domestic pig, wild boar, babirusa, or warthog. This also includes porcines indicated by an arbitrary name referring to their sex, age, or size, such as: sow, boar, hog, gilt, weaner, finisher, fattener, feeder, or (suckling) piglet.

In an embodiment of the method of vaccination according to the invention where the target animal is a porcine, the porcine is preferably selected from a sow, a suckling piglet, a finisher pig, a feeder pig, and a fattener pig.

In an embodiment of the method of vaccination according to the invention wherein the virus is a pathogen of a porcine, the virus is preferably selected from: porcine epidemic diarrhoea virus, porcine reproductive and respiratory syndrome virus, pseudorabies virus, porcine circovirus, porcine parvovirus, classical swine fever virus, african swine fever virus, swine influenza virus, porcine respiratory coronavirus, foot-and-mouth disease virus, transmissible gastro-enteritis virus, porcine cytomegalovirus, porcine rotavirus, porcine poxvirus, and vesicular stomatitis virus.

In an embodiment of the method of vaccination according to the invention wherein the virus is a pathogen of a porcine, the virus is preferably of a species within the Order Nidovirales. More preferably the virus is of a species within the family Arteriviridae or the family Coronaviridae. Even more preferably the virus is of the species PEDV or PRRSV.

In an embodiment of the method of vaccination according to the invention the virus is PEDV and the RP encodes a PEDV spike protein.

In an embodiment of the method of vaccination according to the invention the virus is PRRSV and the RP encodes a PRRSV GP5 protein (Glycoprotein 5, a.k.a.: main envelope protein, or ORF 5 protein).

In an embodiment of the method of vaccination according to the invention where the virus is PEDV, the target animal is a pregnant sow.

In an embodiment of the method of vaccination according to the invention where the virus is PRRSV, the target animal is a pig; the pig can be of any age, from day of birth onward. The pig can be a pregnant sow.

For the method of vaccination according to the invention, the vaccinations are applied in a manner that is compatible with the characteristics of the vaccines and the target animal.

Therefore, in an embodiment of the method of vaccination according to the invention, the vaccine comprising a live attenuated form of a virus is administered by mucosal route. Preferably the mucosal administration is by drinking water, spray, eyedrop, intranasal, or oral route.

In an embodiment of the method of vaccination according to the invention, where the virus is PRRSV, the vaccine comprising a live attenuated form of the PRRSV is preferably administered by parenteral route; more preferably by intramuscular, intradermal or subcutaneous route.

In an embodiment of the method of vaccination according to the invention, the vaccine comprising an RP is administered by parenteral route, by injection into or through the skin. Preferably the parenteral administration is intramuscular, intravenous, intraperitoneal, intradermal, submucosal, or subcutaneous. More preferred route of parenteral administration is by intramuscular, intradermal, or subcutaneous route.

The schedule of the method of vaccination according to the invention is preferably integrated into existing vaccination schedules of other vaccines that the target animal may require, to reduce stress to the target animal and to reduce labor costs. These other vaccines can be administered in a simultaneous, concurrent or sequential fashion, in a manner compatible with their registered use.

The prime and the boost vaccination(s) for the method of vaccination according to the invention are administered at a dose and a volume that is immunologically effective, and that is acceptable for the target animal.

The dose of the live attenuated virus per target animal administration is preferably between 10 and 1×10^8 infectious viruses; this can be measured in pfu, TCID50 or EID50, depending on which method is the most appropriate for the particular virus species.

The dose of the RP per target animal administration is preferably between 1×10^2 and 1×10^12 RPs. These can be measured in TCID50 or RP/ml.

The volume of the vaccinations administered is between 0.01 and 10 ml per target animal administration.

All this is well known in the art.

For the invention, cited ranges also include the stated end points.

As indicated, the method of vaccination according to the invention is especially advantageous when the booster vaccination with the RP encodes an antigen from a virus that is a variant within the species of the live attenuated virus used for the priming vaccination, as this broadens the immune response of the target animal.

Therefore, in an embodiment of the method of vaccination according to the invention at least one viral antigen encoded by the RP is from a virus that is a variant within the species of the live attenuated virus.

For the invention, the term “variant” is used relative to the species of the virus against which the method of vaccination according to the invention aims to protect. Such a variant is thus a virus that is of the same species as the virus that is used in attenuated form for the priming vaccination, but it is not the same virus. In this context, “not the same” can refer to a minor difference e.g. when the variant virus is from a different strain or isolate, or it can refer to a more pronounced difference e.g. when the variant virus differs in respect of its serotype, biotype, pathotype, and/or genotype. The difference may also result from genetic manipulation of one or more of the heterologous genes encoded by the RP.

As described, very advantageous in this regard is also the use of different types of RP in the RP booster vaccine, such as use of an RP that encodes more than one antigen of the virus species for the invention, or use of more than one type of RP, e.g. each encoding different antigens of a virus for the invention, or encoding the same antigen but from different variants of the virus; or even each encoding multiple heterologous antigens.

Therefore, in an embodiment of the method of vaccination according to the invention the vaccine comprising an RP comprises an RP that encodes more than one antigen of the virus species for the invention.

In an embodiment of the method of vaccination according to the invention the vaccine comprising an RP comprises at least one further RP encoding one or more antigens from the virus species for the invention. Preferably the different RP’s encode different antigens of the virus species for the invention. Alternatively, or additionally, the RP’s encode the same antigen but from variants within the virus species for the invention.

In an embodiment of the method of vaccination according to the invention, one or both of the vaccines comprises a further immunostimulatory compound.

Preferably the further immunostimulatory compound is selected from a cytokine, an immunostimulatory nucleic acid comprising an unmethylated CpG, and an adjuvant.

Such immunostimulatory molecules are well-known in the art.

In an embodiment of the method of vaccination according to the invention the immunostimulatory nucleic acid comprising an unmethylated CpG is one or more selected from WO 2012/089.800 (X4 family), WO 2012/160.183 (X43 family), and WO 2012/160.184 (X23 family).

In an embodiment of the method of vaccination according to the invention one or both of the vaccines comprises an adjuvant. Preferably the adjuvant is an oil adjuvant.

In a preferred embodiment one or both of the vaccines comprises a mineral oil adjuvant.

In an alternate preferred embodiment one or both of the vaccines comprises a non-mineral oil adjuvant.

For the invention, "mineral oil" indicates that the respective oil originates from a mineral source, typically from petroleum; a "non-mineral oil" is of synthetic-, semi-synthetic-, animal- or vegetable origin.

In an embodiment of the method of vaccination according to the invention, the vaccine comprising an RP comprises an oil adjuvant, which oil adjuvant comprises a mineral oil and one or more non-mineral oils.

More preferably the oil adjuvant of the RP booster vaccine comprises a liquid paraffin oil and Vitamin E-acetate. Even more preferably the vaccine comprising an RP comprises an Xsolve™ adjuvant.

In an embodiment of the method of vaccination according to the invention, the vaccine comprising an RP comprises an oil adjuvant, which oil adjuvant comprises more than one non-mineral oil. More preferably the oil adjuvant of the RP booster vaccine comprises squalane and Vitamin E-acetate. Even more preferably the vaccine comprising an RP comprises a SVEA™ adjuvant.

For the invention: liquid paraffin oil is CAS number: 8042-47-5; squalane is CAS number 111-01-3; and vitamin E acetate is CAS number: 58-95-7. In an embodiment vitamin E acetate is dl-α-tocopherol-acetate.

In an embodiment of the method of vaccination according to the invention, the oil adjuvant is formulated with one or both of the vaccines as an emulsion of water and oil. Preferably the emulsion is an oil-in-water emulsion. In an alternate preferred embodiment the emulsion is a water-in-oil emulsion.

In an embodiment of the method of vaccination according to the invention where the vaccine comprising an RP comprises an oil adjuvant, the adjuvant is preferably combined with the RP shortly before administration, e.g. within 1 day, 6 hours, 4 hours, or within 2 hours before administration, in this order of preference.

In the method of vaccination according to the invention one or both of the vaccines may comprise one or more further excipients that assist e.g. in the formulation, the stabilization, or the delivery of that vaccine. Examples are stabilizers, preservatives, and viscosity modifiers.

In an embodiment of the method of vaccination according to the invention one or both of the vaccines comprises a further excipient selected from stabilizers, preservatives, and viscosity modifiers.

Preferred stabilizer is one or more selected from dextran, glycerol, gelatin, amino acids, antioxidants, and buffers.

Preferred preservative is one or more selected from thiomersal, phenoxyethanol, formaldehyde, and antibiotics.

Preferred viscosity modifier is one or more selected from polyvinyl pyrrolidone and Gantrez™.

In an embodiment of the method of vaccination according to the invention the vaccine comprising a live attenuated form of a virus comprises a viscosity modifier selected from a polyvinyl pyrrolidone and a Gantrez™.

For the invention, Gantrez™ (Ashland, Covington, KY, USA) is a family of polymers and copolymers of vinyl ether.

In an embodiment of the method of vaccination according to the invention the vaccination with the vaccine comprising a live attenuated form of a virus is followed by the vaccination with the vaccine comprising an RP within a period of time that is between 1 week and 80 years.

Preferably the period of time is between 1 week and 3 years, between 1 week and 2 years, between 1 week and 1 year, between 1 week and 6 months, between 1 week and 3 months, between 1 week and 2 months, between 1 week and 1 month, between 1 week and 4 weeks, between 1 week and 3 weeks, or even between 1 week and 2 weeks, in this order of preference.

Preferably the period of time is selected from: 2 years, 1 year, 6 months, 4 months, 3 months, 2 months, 1 month, 4 weeks, 3 weeks, 2 weeks and 1 week.

In a preferred embodiment of the method of vaccination according to the invention the vaccination with the vaccine comprising a live attenuated form of a virus is followed by the vaccination with the vaccine comprising an RP within a period of time of at least one week. More preferably within a period selected from: at least two weeks, at least three weeks, at least 4 weeks, at least 1 month, at least 2 months, at least 3 months, at least 6 months, at least 1 year, and at least 2 years.

In an embodiment of the method of vaccination according to the invention the virus on which the RP vaccine is based is an Alphavirus, and preferably the species is VEEV.

Preferably the VEEV is from the strain TC-83.

In an embodiment of the method of vaccination according to the invention one or more of the conditions apply, selected from the group consisting of:

the target animal is an animal of veterinary relevance. Preferably the animal of veterinary relevance is an animal selected from a bovine, porcine, caprine, ovine, cervine, canine, feline, equine, and avian. More preferably the animal is selected from a bovine, porcine, ovine, canine, feline, equine, and avian. Even more preferably the animal is selected from a porcine, canine, feline, and avian. Still even more preferably the animal is selected from a porcine and avian. Most preferred the animal is a porcine;

the virus is a virus of relevance to veterinary practice. Preferably the virus is an animal pathogen. More preferably the virus is a pathogen of an animal selected from a bovine, porcine, caprine, ovine, cervine, canine, feline, equine, and avian. More preferably the virus is a pathogen of an animal selected from a bovine, porcine, ovine, canine, feline, equine, and avian. Even more preferably the virus is a pathogen of an animal selected from a porcine, canine, feline, and avian. Still even more preferably the virus is a pathogen of an animal selected from a porcine and avian. Most preferred the virus is a pathogen of a porcine;

the target animal is a porcine, the porcine is preferably selected from a sow, a suckling piglet, a finisher pig, a feeder pig, and a fattener pig;

the virus is a pathogen of a porcine, the virus is preferably selected from: porcine epidemic diarrhoea virus, porcine reproductive and respiratory syndrome virus, pseudorabies virus, porcine circovirus, porcine parvovirus, classical swine fever virus, african swine fever virus, swine influenza virus, porcine respiratory coronavirus, foot-and-mouth disease virus, transmissible gastro-enteritis virus, porcine cytomegalovirus, porcine rotavirus, porcine poxvirus, and vesicular stomatitis virus;

the virus is preferably of a species within the Order Nidovirales. More preferably the virus is of a species within the family Arteriviridae or the family Coronaviridae. Even more preferably the virus is of the species PEDV or PRRSV;

the virus is PEDV and the RP encodes a PEDV spike protein;

the virus is PRRSV and the RP encodes one or more PRRSV glycoproteins, such as for example a GP5 protein;

the virus is PEDV, the target animal is a pregnant sow;

the virus is PRRSV, the target animal is a pig; the pig can be of any age, from day of birth onward. The pig can be a pregnant sow;

the mucosal administration is by drinking water, spray, eyedrop, intranasal, or oral route;

the virus is PRRSV, the vaccine comprising a live attenuated form of the PRRSV is preferably administered by parenteral route; more preferably by intramuscular, intradermal or subcutaneous route;

the vaccine comprising an RP is administered by parenteral route, by injection into or through the skin. Preferably the parenteral administration is intramuscular, intravenous, intraperitoneal, intradermal, submucosal, or subcutaneous. More preferred route of parenteral administration is by intramuscular, intradermal, or subcutaneous route;

at least one viral antigen encoded by the RP is from a virus that is a variant within the species of the live attenuated virus;

the vaccine comprising an RP comprises an RP that encodes more than one antigen of the virus species for the invention;

the vaccine comprising an RP comprises at least one further RP encoding one or more antigens from the virus species for the invention. Preferably the different virus RNA RP's encode different antigens of the virus species for the invention. Alternatively, or additionally, the RP's encode the same antigen but from variants within the virus species for the invention;

one or both of the vaccines comprises a further immunostimulatory compound. Preferably the further immunostimulatory compound is selected from a cytokine, an immunostimulatory nucleic acid comprising an unmethylated CpG, and an adjuvant. Preferably the immunostimulatory nucleic acid comprising an unmethylated CpG is one or more selected from WO 2012/089.800 (X4 family), WO 2012/160.183 (X43 family), and WO 2012/160.184 (X23 family);

one or both of the vaccines comprises an adjuvant. Preferably the adjuvant is an oil adjuvant;

one or both of the vaccines comprises a mineral oil adjuvant. In an alternate preferred embodiment one or both of the vaccines comprises a non-mineral oil adjuvant;

the vaccine comprising an RP comprises an oil adjuvant, which oil adjuvant comprises a mineral oil and one or more non-mineral oils. More preferably the oil adjuvant of the vaccine comprising an RP comprises a liquid paraffin oil and Vitamin E-acetate. Even more preferably the vaccine comprising an RP comprises an Xsolve™ adjuvant;

the vaccine comprising an RP comprises an oil adjuvant, which oil adjuvant comprises more than one non-mineral oil. More preferably the oil adjuvant of the vaccine comprising an RP comprises squalane and Vitamin E-acetate. Even more preferably the vaccine comprising an RP comprises a SVEA™ adjuvant;

vitamin E acetate is dl-α-tocopherol-acetate;

the oil adjuvant is formulated with one or both of the vaccines as an emulsion of water and oil. Preferably the emulsion is an oil-in-water emulsion. In an alternate preferred embodiment the emulsion is a water-in-oil emulsion;

the adjuvant is combined with the RP shortly before administration, e.g. within 1 day, 6 hours, 4 hours or 2 hours before administration;

one or both of the vaccines comprises a further excipient selected from stabilizers, preservatives, and viscosity modifiers. Preferred stabilizer is one or more selected from dextrane, glycerol, gelatin, amino acids, antioxidants, and buffers. Preferred preservative is one or more selected from thiomersal, phenoxyethanol, formaldehyde, and antibiotics. Preferred viscosity modifier is one or more selected from polyvinyl pyrrolidone and Gantrez™;

the vaccine comprising a live attenuated form of a virus comprises a viscosity modifier selected from polyvinyl pyrrolidone and Gantrez™;

the vaccination with the vaccine comprising a live attenuated virus is followed by the vaccination with the vaccine comprising an RP within a period of time that is between 1 week and 80 years. Preferably the period of time is between 1 week and 3 years, between 1 week and 2 years, between 1 week and 1 year, between 1 week and 6 months, between 1 week and 3 months, between 1 week and 2 months, between 1 week and 1 month, between 1 week and 4 weeks, between 1 week and 3 weeks, or even between 1 and 2 weeks, in this order of preference. Preferably the period of time is selected from: 2 years, 1 year, 6 months, 4 months, 3 months, 2 months, 1 month, 4 weeks, 3 weeks, 2 weeks and 1 week;

the vaccination with the vaccine comprising a live attenuated form of a virus is followed by the vaccination with the vaccine comprising an RP within a period of time of at least one week. More preferably within a period selected from: at least two weeks, at least three weeks, at least 4 weeks, at least 1 month, at least 2 months, at least 3 months, at least 6 months, at least 1 year, and at least 2 years; and the species of the virus of the vaccine comprising an Alphavirus RNA RP is VEEV. Preferably the VEEV is from the strain TC-83.

In an embodiment of the method of vaccination according to the invention the target animal is a porcine, the virus is PEDV, the porcine is a pregnant sow, the vaccine comprising a live attenuated form of a virus comprises a viscosity modifier, and the virus of the vaccine comprising an Alphavirus RNA RP is VEEV.

In an embodiment of the method of vaccination according to the invention the target animal is a porcine, the virus is PRRSV, the Avirus of the Vaccine comprising an Alphavirus RNA RP is VEEV, and the Vaccine comprising the RP comprises an oil adjuvant.

The method for the vaccination according to the invention can also be worded in a different format e.g. by way of the vaccination regimen it embodies, or by the medical use of each of the vaccines used in this method.

Therefore in a further aspect the invention relates to a prime-boost vaccination regimen for protecting a target animal against infection or disease caused by a virus, wherein the vaccination regimen comprises the administration to said target animal of a vaccine comprising a live attenuated form of said virus, followed by the administration to said target animal of a vaccine comprising an RP encoding one or more antigens from said virus.

In a further aspect the invention relates to a vaccine comprising a live attenuated form of a virus for use in a prime-boost vaccination regimen to protect a target animal against infection or disease caused by said virus, said regimen comprising:
   a vaccination with the vaccine comprising a live attenuated form of a virus, followed by
   a vaccine comprising an RP encoding one or more antigens from said virus.

In a further aspect the invention relates to a vaccine comprising an RP encoding one or more antigens from a virus, for use in a prime-boost vaccination regimen to protect a target animal against infection or disease caused by said virus, said regimen comprising:
   a vaccination with a vaccine comprising a live attenuated form of said virus, followed by
   a vaccination with the vaccine comprising an RP.

In a further aspect the invention relates to the use of a live attenuated form of a virus for the manufacture of a vaccine for the protection of a target animal against infection or disease caused by said virus, whereby said vaccine is administered in a prime-boost vaccination regimen, said regimen comprising:
   the administration of the vaccine comprising a live attenuated form of a virus, followed by
   the administration of a vaccine comprising an RP encoding one or more antigens from said virus.

And in a further aspect the invention relates to the use of an RP encoding one or more antigens from a virus, for the manufacture of a vaccine for the protection of a target animal against infection or disease caused by said virus, whereby said vaccine is administered in a prime-boost vaccination regimen, said regimen comprising:
   the administration of a vaccine comprising a live attenuated form of said virus, followed by
   the administration of the Vaccine comprising an RP.

In preferred embodiments of these further aspects of the invention one or more or all of the features of these further aspects such as the prime-boost vaccination regimen, the virus, the vaccine comprising a live attenuated virus, the vaccine comprising an RP, the time interval between the prime and the boost vaccination, the protection, the target animal, the infection, the disease, and the administration, are all as defined in any one or more of the embodiments as described herein.

For the invention, the use of the live attenuated form of a virus, or of the RP for the manufacture according to the invention, is performed in a way that allows the medical use of the vaccines produced.

Commonly this regards using equipment and ingredients that are pharmaceutically acceptable, and complying with quality regulations such as good manufacturing practice standards. This implies that the various stages of the manufacturing process will be monitored by adequate tests, for instance by immunological tests for the quality and quantity of the antigens; by microbiological tests for sterility, and absence of extraneous agents; and ultimately by studies in animals for confirming vaccine efficacy and safety. After completion of these tests the vaccine product can be released for sale.

All these are well known to a skilled person, and general techniques and considerations that apply to the preparation of vaccines are described for instance in Governmental regulations such as the European Pharmacopoeia, the 9 and 21 CFR, and in handbooks such as P. Pastoret et al. (supra), and "Remington: the science and practice of pharmacy" (2000, Lippincot, USA, ISBN: 683306472).

The vaccines for use in the method of vaccination according to the invention, the vaccine comprising a live attenuated form of a virus and the vaccine comprising an RP, can be supplied to the market separately and can then be used in the method of vaccination according to the invention. Alternatively the vaccines can be supplied in a combination which facilitates their use in the method of vaccination according to the invention.

Therefore in a further aspect, the invention relates to a kit of parts comprising at least two containers, wherein at least one container comprises a vaccine comprising a live attenuated form of a virus as defined for the invention, and at least one container comprises a vaccine comprising an RP encoding a viral antigen as defined for the invention.

In preferred embodiments of the kit of parts of the present invention, one or more or all features of the kit of parts are as defined in any one or more of the embodiments as described herein.

In a preferred embodiment the at least one container comprising the vaccine comprising a live attenuated form of a virus, is comprising said vaccine as a lyophilizate which can be diluted with a diluent shortly before administration.

In a preferred embodiment the at least one container comprising the vaccine comprising RP is comprising said vaccine as a lyophilizate, which can be diluted with a diluent shortly before administration.

In an alternate embodiment the at least one container comprising the vaccine comprising an RP, is comprising said vaccine in an aqueous solution; the aqueous solution preferably comprising a buffer; and the aqueous solution with said vaccine is preferably kept cooled or frozen until use. In an embodiment the aqueous solution with said vaccine is a solution of a reconstituted RP, generated from the admixing of the RP lyophilizate and a suitable aqueous diluent.

In the embodiment wherein the at least one container comprises the vaccine comprising an RP as a lyophilizate, the kit of parts according to the invention can comprise a further container, which further container can comprise a suitable diluent for reconstituting the lyophilized vaccine comprising an RP. In a preferred embodiment the diluent is an aqueous solution, preferably comprising a buffer and/or a stabilizer and water of pharmaceutically acceptable quality.

In an alternate preferred embodiment, the diluent is an oil-in-water emulsion for reconstituting and adjuvating the vaccine comprising an RP.

In an embodiment of the kit of parts according to the invention, the kit comprises instructions for use of the kit and/or of its component parts. In preferred embodiments the instructions for use are provided on or with one or more of the component parts of the kit; or are provided by way of a reference to instructions in electronic form, such as information viewable on, or downloadable from an internet website from the manufacturer, or the distributor of the kit.

In an embodiment the kit of parts is a box comprising the at least two containers, and comprising instructions for use which are displayed on an information carrier (e.g. a card, or a leaflet) comprised on, with, or within the box.

In an embodiment of the kit of parts, the kit may also be an offer of the component parts (relating to commercial sale), for example on an internet website, for use in a method of vaccination according to the invention.

It is well within reach of a skilled person to further optimize the method, vaccines, uses, regimen and kit of the invention. Generally this involves the fine-tuning of the efficacy of the vaccines and their administration to adapt to specific conditions that may be applicable. This can be done by adapting the dose, volume, antigen content or adjuvant of the vaccines, or by adapting the route or method of the administration. All such finetuning can be done using routine methods and materials known in this field.

In any of the above described embodiments of the current invention, the use of an Alphavirus RNA replicon particle is preferred.

The invention will now be further described by the following, non-limiting, examples.

EXAMPLES

1. Example 1: Homologous Grime-Boost PRRSV Vaccination

The existing PRRSV live vaccine Porcilis® PRRS is based on a European isolate of PRRSV, strain DV, a genotype 1 PRRSV. This was found to sometimes lack in efficacy when tested against a heterologous challenge strain, which is a problem common to all vaccines of attenuated live PRRSV. Different ways were investigated to improve this vaccination efficacy, such as a homologous prime-boost vaccination regimen.

In a vaccination-challenge experiment, 3 groups were used with 16 pigs of approximately 5 weeks old, and PRRSV-antibody negative at the day of $1^{st}$ vaccination. Two groups received a vaccination with live attenuated virus Porcilis PRRS, either once, or two times with a 2-week interval. One group remained unvaccinated. All pigs received a challenge infection with PRRSV of a recent German genotype 1 isolate, at 4.5 weeks after the vaccination, respectively after the first vaccination. Challenge dose was 5.3 Log 10 TCID50 of virus, in 2 ml per animal (1 ml in each nostril). Blood samples were taken at the days of vaccination and at 0, 4, 7, 10, 14 and 20 days post challenge. PRRSV viremia was determined as cpe on PAM cells, all as described below.

Figure 1:
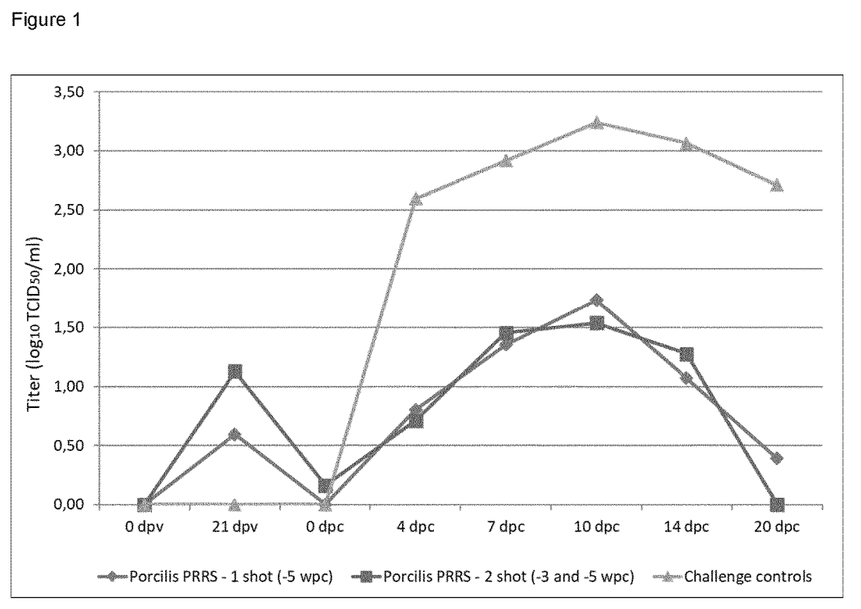

FIG. 1 presents the viremia results of the 3 groups. As can be clearly seen, there was no significant difference in the effect of using one or two vaccinations with an attenuated live PRRSV vaccine.

Consequently, for PRRSV, the use of a homologous prime-boost vaccination regimen cannot improve the immune-protection of the single vaccination.

2. Example 2: PRRSV—Prime-Boost Vaccination, Initial Experiments

2.1. Introduction

This experiment applied the method of vaccination according to the invention, with a variant in the booster vaccination: the vaccine of the live attenuated virus used was Porcilis® PRRS, which is of PRRSV type 1, strain DV, and the vaccine comprising an Alphavirus RNA RP, as well as the challenge virus used, were based on PRRSV type 1 strain Sc3.

The Alphavirus RNA RP used were based on VEEV strain TC-83, and expressed more than one viral antigen: one type of RP (here: RP1) was made to encode the PRRSV strain Sc3 genes: E, GP2, GP3 and GP4, leading to the expression of the native E-GP2-GP3-GP4 tetramer. Another type of RP (here: RP2) was made to encode the PRRSV strain Sc3 genes: GP5 and M, leading to the expression of the native GP5-M dimer. In each case (RP1 and RP2), each of the heterologous genes were under the transcriptional control of their own subgenomic promoter sequence. In RP1, four separate subgenomic promoter sequences were present; in RP2, two subgenomic promoter sequences were present.

2.2. Study Design 40 piglets seronegative for anti-PRRSV antibodies were divided over 4 groups of 10 animals. When the piglets of groups 1 to 3 were about 5 weeks old they were given a priming vaccination via the intramuscular (IM) route with the live attenuated virus vaccine Porcilis® PRRSV; animals of group 4 served as non-vaccinated control animals. At 3 weeks after the priming vaccination, groups 2 and 3 received their booster vaccination with vaccine comprising 2 types of Alphavirus RNA RP. At about 4.5 weeks post priming vaccination, i.e. 11 days post booster vaccination, all animals were challenged with contemporary virulent genotype 1 strain Sc-3, by intranasal route. Blood samples were collected on the day of priming vaccination and 7, 15, and 23 days thereafter, as well as on the day of challenge (=day 32 dpv) and 4, 7, 11, 17 and 21 days thereafter. Serum was isolated from these samples, and the samples obtained after challenge were used to determine the vaccine efficacy of the different vaccinations by measuring the challenge strain's viremia.

2.3. Materials and Methods

Treatment:

The recommended route of vaccination for Porcilis® PRRS was used, i.e. intramuscular administration, also for the vaccine comprising an Alphavirus RNA RP. For the challenge inoculation a natural route of infection was used, the nasal route. Blood samples were taken to monitor the relevant parameters of PRRSV infection: viremia and serology.

Test Articles:

Challenge virus was PRRSV strain Sc-3, diluted to $0.5\times10^{\wedge}5.0$ TCID50/ml.

Diluent for the freeze dried Porcilis® PRRS vaccine was 10 mM PBS buffer. This was applied shortly before use to obtain a titer of $0.5\times10^{\wedge}5.0$ TCID50/ml.

Titrations were done on primary porcine alveolar macrophages (PAMs) by reading cpe after 5-7 days.

Diluent for the RP was Xsolve™ 50 oil-in-water emulsion, also applied shortly before use, to arrive at a titer of $0.5\times10^{\wedge}8.0$ TCID50/ml for each of the vaccines comprising Alphavirus RNA RP1 or RP2.

When the RP are categorized as GMO, all materials, samples, and animals need to be handled and kept in facilities at the appropriate level of biological containment.

Test Animals:

Standard piglets, about 5 weeks old at day of vaccination, of mixed sex, and negative for antibodies against PRRSV until vaccination. The piglets had 5 days of acclimatization between transportation to the test facility and day of vaccination. Only clinically healthy pigs were used; pigs were identified using numbered ear tags. All animals were observed daily during the experiment for general health. All observations were recorded, and the responsible veterinarian was consulted when required.

All vaccinations were given IM at 2 ml/animal, the challenge was given IN at 2 ml/animal.

TABLE 1

Experimental outline of Example 2

| Group | # of pigs | Vaccination (prime) | | | Vaccination (boost at 3 wpv) | | | Challenge (at ~4.5 wpv) | | |
|---|---|---|---|---|---|---|---|---|---|---|
| | | Vaccine | Dose | Adjuvant | Vaccine | Dose | Adjuvant | Strain | Dose | Route |
| 1 | 10 | Porcilis PRRS | $1 \cdot 10^5$ TCID50 | — | — | | | Sc-3 | $1 \cdot 10^5$ TCID50 | IN |
| 2 | 10 | Porcilis PRRS | $1 \cdot 10^5$ TCID50 | — | RP1 + RP2 | Per RP: $1 \cdot 10^8$ TCID50 | X-Solve50 | Sc-3 | $1 \cdot 10^5$ TCID50 | IN |
| 3 | 10 | RP1 + RP2 | Per RP: $1 \cdot 10^8$ TCID50 | X-Solve50 | RP1 + RP2 | Per RP: $1 \cdot 10^8$ TCID50 | X-Solve50 | Sc-3 | $1 \cdot 10^5$ TCID50 | IN |
| 4 | 10 | — | | | — | | | Sc-3 | $1 \cdot 10^5$ TCID50 | IN |

Sampling

Blood samples were taken from the jugular vein at 0, 7, 15, and 23 days post priming vaccination (dpv), and at 0 (=32 dpv), 4, 7, 11, 17, and 21 days post challenge (dpc). The last blood sample was taken during euthanization at the end of the experiment. Blood was collected in a vacutainer without anti-coagulant. The blood samples were allowed to coagulate at room temperature for 1 hr., then centrifuged for 10 minutes at 3000×g. and serum was collected and stored frozen below −20° C. until use.

Viremia Detection

Viremia of PRRSV (both of vaccine comprising a live attenuated form of a virus and of challenge virus) was detected by quantification of PRRSV RNA in serum by real-time RT-qPCR using primer sets specific for PRRSV genotype 1, and the iTaq™ Universal SYBR® Green One-Step Kit (BioRad).

Serology

Sera were tested for antibodies against PRRSV using a commercial ELISA kit: IDEXX™ PRRS X3 (IDEXX Laboratories, Westbrook, ME, USA). Serum was incubated in recombinant PRRSV antigen-coated micro-titration wells. Bound PRRSV-specific antibodies were then detected using horseradish peroxidase-conjugated anti-porcine antibody and a chromogen. Results were calculated as sample to positive (S/P) ratio. Samples with S/P ratios≥0.4 were classified as positive and samples with S/P ratios<0.4 were classified as negative for PRRSV-specific antibodies.

2.4. Results and Conclusions

The experiment was considered valid as all serum samples prior to vaccination were PRRSV-Ab negative, and the serum samples of group 4 were PRRSV-Ab negative until challenge.

Figure 2:
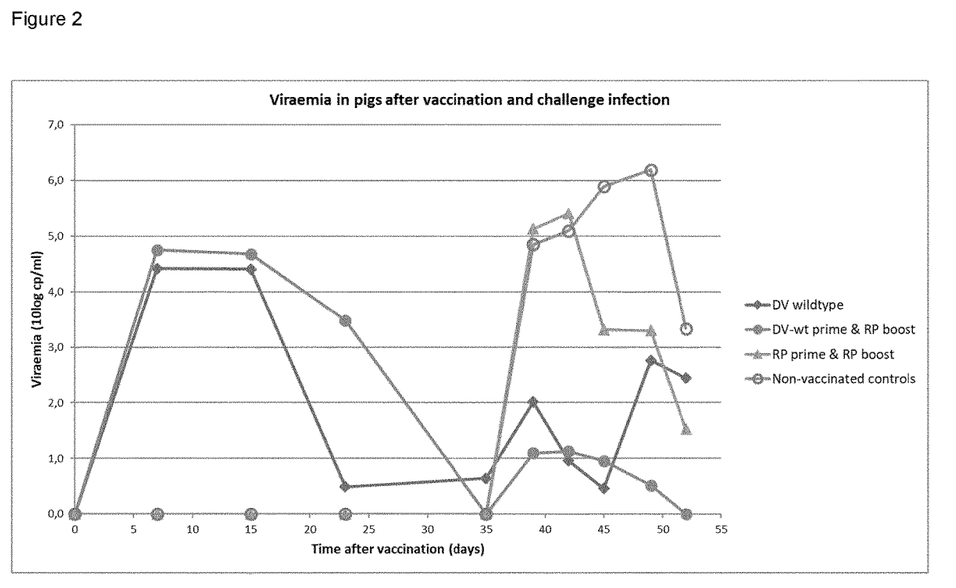

Results of viremia determinations are presented in FIG. 2, which represents the qPCR scores compiled per group.

Non-vaccinated pigs (group 4) showed the highest levels of PRRS virus in their serum, which was as expected. Also as expected, the prime-booster vaccination with the two Alphavirus RNA RPs at 21 dpv does not result in the detection of PRRSV viremia levels in the serum (e.g. see group 3, FIG. 2).

In animals receiving both a priming and a booster vaccination with vaccine comprising Alphavirus RNA RP1 and RP2 (group 3), the viremia levels observed were almost equally high as the levels found in the non-vaccinated animals.

Clearly a homologous prime-boost regimen with a vaccine comprising Alphavirus RNA RP did not provide adequate protection for PRRSV, even when these encoded multiple antigens of the challenge virus.

A good reduction in viremia was provided by the live attenuated vaccine (group 1). However, the group receiving vaccinations according to the heterologous prime-boost vaccination regimen of the invention (group 2) showed the best protection against challenge infection of all; i.e. had the lowest levels of detectable PRRSV in serum samples after challenge at all times.

3. Example 3: PRRSV—Prime-Boost Vaccination, Extended Experiment 3.1. Introduction Further experiments were arranged, in order to repeat and expand on the remarkable results found in the experiments described in Example 2. In this set-up, groups were added to test the effect of separate vaccines comprising Alphavirus RNA RP1 or RP2 as booster vaccination. In addition one group was added to test the reverse order of the vaccinations in the method of vaccination according to the invention.

3.2. Study Design

The study design in this example was essentially the same as that in Example 2, except for the extra test groups. The experimental outline of Example 3 is summarized in Table 2. All groups received the challenge infection with PRRSV strain Sc-3 at 5 weeks after the priming vaccination, i.e. at 2 weeks after the booster vaccination.

TABLE 2

Experimental outline of Example 3

| | Vaccination | |
|---|---|---|
| Group | priming | booster |
| 1 | Porcilis PRRS | — |
| 2 | | RP1 + RP2 (Xsolve50) |
| 3 | | RP2 (Xsolve50) |
| 4 | | RP1 (Xsolve50) |
| 5 | RP1 + RP2 (Xsolve50) | Porcilis PRRS |
| 6 | — | — |

3.3. Materials and Methods

Vaccinations and challenges were largely the same as applied in Example 2. Regarding timing the challenge was at 5 weeks after priming vaccination, instead of at 4.5 weeks in Example 2. Two groups were added, groups 3 and 4, receiving the single vaccines comprising Alphavirus RNA RP1 or RP2 as booster vaccination.

3.4. Results and Conclusions

Figure 3:
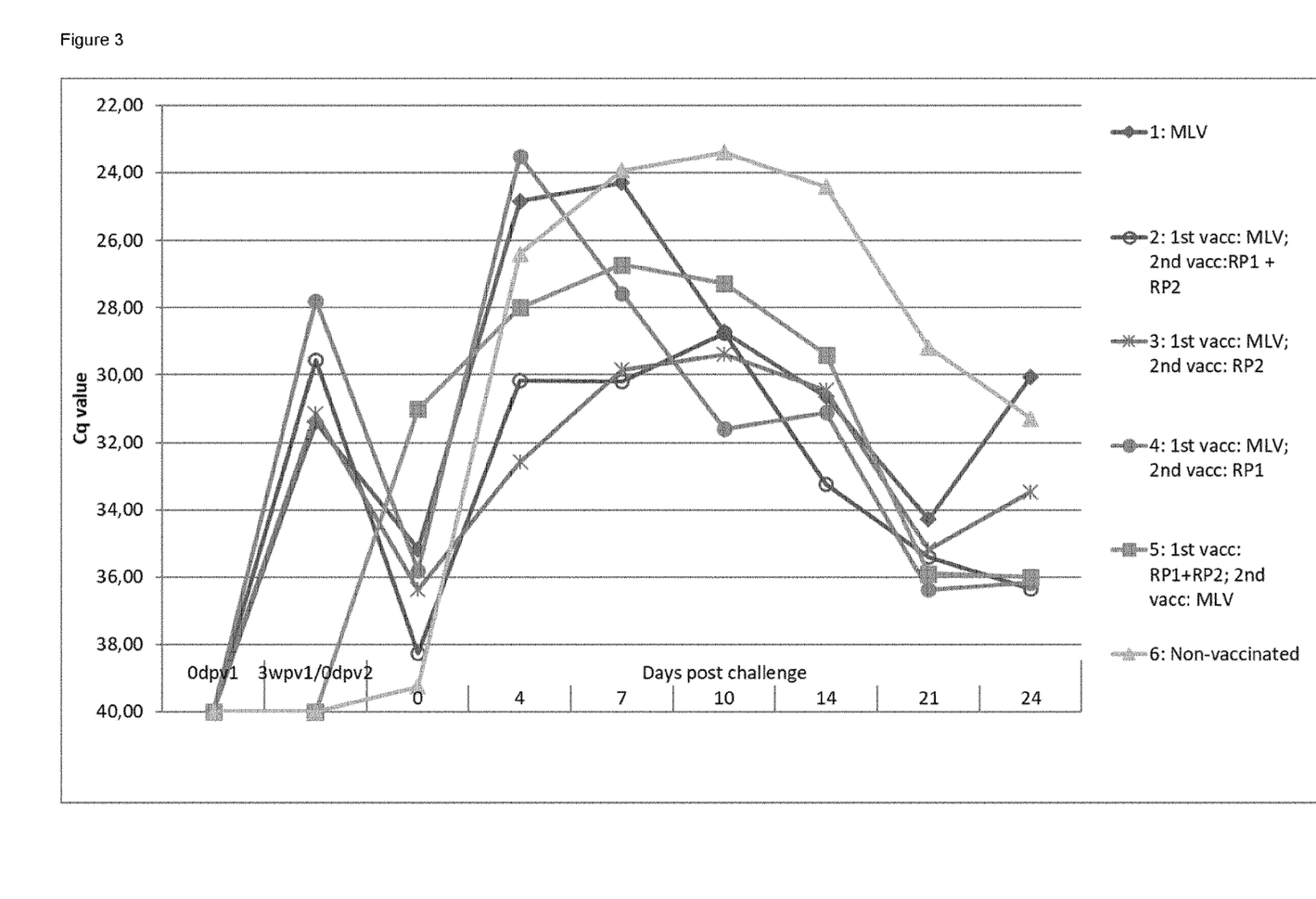

Results are presented in FIG. 3. The best time point to compare results is the viremia (in Ct values) at 4 days post challenge.

Again the test was valid, based on seronegativity for anti-PRRSV-antibodies prior to vaccination. Also, the unvaccinated group 6 responded as expected, post challenge. A similar viremia as in group 6, was detected in the groups receiving a single vaccination with attenuated live virus (MLV: modified live vaccine; group 1) and the group 4, receiving a boost vaccination with RP1 (E-GP2-3-4) vaccine. Slightly better than the unvaccinated group, was the group 5, receiving the vaccinations of the method of vaccination according to the invention but in reversed order.

However, best of all were groups receiving as booster a vaccine comprising Alphavirus RNA RP2 alone or in combination with RP1. Group 2, receiving as booster a vaccine comprising Alphavirus RNA RP1 and RP2 had much reduced viremia post challenge, but group 3, receiving as booster vaccination the vaccine comprising Alphavirus RNA RP2 after the vaccine comprising live attenuated PRRSV had the lowest viremia overall.

The difference in viremia at 4 days post challenge between groups 3 (method of vaccination according to the invention, with RP2) and 5 (reversed order) is about 5 Cq points, which corresponds with a difference in virus load of 2^5. Thus challenge virus viremia could be reduced with a factor of 32-fold, when applying the correct method of vaccination according to the invention.

Similarly, when considering the improvement in vaccine protection between single vaccine of live attenuated virus (group 1), and group 3 (method of vaccination according to the invention), the difference in viremia detected is 8 Cq points, a factor 256 less viremia, which is highly significant for the field, in terms of control of disease and spread of PRRSV in the herd.

Also this represents a broadening of the immune protection from the PRRSV DV strain of the priming vaccination, to the PRRSV Sc3 strain of the challenge virus, by using vaccine comprising an Alphavirus RNA RP encoding Sc3 genes.

4. Example 4: PEDV—Prime-Boost Vaccination Experiments

In line with the experiments performed for PRRSV, similar experiments were performed using a method of vaccination according to the invention to protect swine against infection with PEDV.

4.1. Introduction

In this experiment, the efficacy of vaccination of pregnant sows was tested, in order to protect their offspring after suckling, against PEDV infection and disease, using a method of vaccination according to the invention. For the vaccine comprising a live attenuated virus was used the PEDV strain S-INDEL Iowa 106. This is one of the two types of the emerging strains of PEDV (Lin et al., 2016, Virus Res., vol. 226, p. 20-39). The vaccine of the Alphavirus RNA RP comprised an RP encoding the spike protein of a virulent US isolate of PEDV, which is a non-S-INDEL strain.

4.2. Study Design 14 pregnant sows were randomized into four treatment groups including 3 vaccinated groups and one non-vaccinated control group (group 4). All vaccinated sows (groups 1-3) received three vaccinations at 6, 3 and 1 week prior to farrowing. The vaccine for the first and second vaccination for sows in groups 2 and 3 was a vaccine comprising a live attenuated virus of PEDV strain S-INDEL Iowa 106, blended with one of two different mucosal adhesives. Sows in group 1 received two priming vaccinations with an RP vaccine encoding the spike gene of a PEDV non-S-INDEL strain. As the 3$^{rd}$ vaccination, all sows in groups 1-3 received a booster vaccination with the vaccine of the Alphavirus RNA RP encoding the PEDV-spike gene. An overview of the experimental groups is given in Table 3.

Suckling piglets born from the different sow groups were challenged intra-gastrically with a virulent PEDV strain. Vaccine efficacy was measured by the ability of the vaccine to reduce piglet mortality and maintain weight gain in the piglets. The immune response in respect of PEDV-specific, maternally derived antibodies (MDA) in piglets was also assessed.

TABLE 3

Experimental outline of Example 4

| Group | N | Vaccine | Dose (TCID or copy) | Mucosal adhesive | Vaccination | Route | Weeks to farrow |
|---|---|---|---|---|---|---|---|
| 1(PED-RP) | 4 | RP | 10^8 copies | No | 1$^{st}$ | IM | 6 |
|  |  |  |  |  | 2$^{nd}$ | IM | 3 |
|  |  |  |  |  | 3$^{rd}$ | IM | 1 |
| 2 (Gantrez) | 4 | MLV | 10^6 TCID50 | Gantrez | 1$^{st}$ | Oral | 6 |
|  |  |  |  |  | 2$^{nd}$ | Oral | 3 |
|  |  | RP | 10^8 copies | No | 3$^{rd}$ | IM | 1 |
| 3 (PVP) | 4 | MLV | 10^6 TCID50 | PVP | 1$^{st}$ | Oral | 6 |
|  |  |  |  |  | 2$^{nd}$ | Oral | 3 |
|  |  | RP | 10^8 copies | No | 3$^{rd}$ | IM | 1 |
| 4 (Control) | 2 | — | — | — | — | — | — |

4.3. Materials and Methods

Test Articles:
Vaccine of Alphavirus RNA RP:

The vaccine comprising an Alphavirus RNA RP was based on a replicon construct from VEEV strain TC-83. This was constructed to comprise the coding sequence of the spike protein of US virulent PEDV strain AH2012 (see GenBank Accession number KC210145). This was formulated at $10^{\wedge}8$ RP/ml, for 1 ml doses, without adjuvant, for IM vaccination.

The RP was titrated on Vero cell monolayer cultures in 96 well plates, in 10-fold serial dilutions. The plates were incubated at 37° C. for 18-24 hr. Next the plates were washed, fixed and stained with primary antibody followed by a conjugated secondary antibody. The cells are examined using a fluorescence microscope. The individual antigen-positive cells are counted. The titer, expressed as RP/ml, is calculated from the known dilution and inoculation volumes, and averaged between the duplicate wells.

Attenuated Live Vaccine:
Group 2 Vaccine:

$10^{\wedge}6$ TCID50 per dose of PEDV S-INDEL Iowa 106, passage 36 was mixed with Gantrez™ (1:1 v/v ratio), 5% Sucrose, and 20 mM HEPES pH 7.3, shortly prior to vaccination orally.

Group 3 Vaccine:

$10^{\wedge}6$ TCID50 per dose of PEDV S-INDEL Iowa 106, passage 36 was mixed with polyvinyl pyrrolidone (PVP) (1:1 v/v ratio) 5% Sucrose and 20 mM HEPES pH 7.3, shortly prior to vaccination orally.

The PEDV S-INDEL Iowa 106 virus was titrated on 96 well plates with confluent Vero cells. Plates were incubated at 37° C. with 5% $CO_2$ and observed daily for cytopathic effect post infection for 2-3 days and/or tested using IFA staining with swine anti-PEDV specific antibody (USDA-NVSL, Ames, Iowa) followed by a FITC conjugated secondary antibody at the end of the incubation period. PEDV titers were calculated as Log 10 TCID50 per mL, using the Spearman/Karber method.

Challenge Virus:

Challenge was given intra-gastrically to suckling pigs at 3 to 5 days of age, with PEDV strain Colorado 2013 isolate, at $10^{\wedge}5$ TCID50 per pig.

Challenge virus was titrated on Vero cells, similar to PEDV live attenuated virus.

Fecal Shedding

PEDV RNA extraction and detection of PEDV viremia was done using qRT-PCR, according to Chen et al. (2014, J. Clin. Microbiol., vol. 52, p. 234-243). MagMAX™ Pathogen RNA/DNA Kit (Life Technologies, Carlsbad, CA, USA) and a Kingfisher 96 instrument (Thermo Scientific, Waltham, MA, USA) were used following the instructions of the manufacturers. The qRT-PCR was performed using a Path-ID Multiplex One-Step RT-PCR kit (Life Technologies) and conducted on an ABI 7500 Fast Instrument™ (Life Technologies).

Serology

PEDV-specific neutralizing antibodies in serum, colostrum and milk in sows and passive antibodies in piglet sera was determined by fluorescent focus neutralization (FFN) test.

PEDV antibody in sera against the S1 part of the PEDV spike protein of the challenge PEDV strain were determined in an antibody ELISA: micro-titration plates were coated with 100 µl of a PEDV spike protein (recombinant S1 dimer from PEDV strain Colorado 2013; 0.25 µg/ml). Sera were diluted 1:900 in PBS/1 BSA and added to the coated wells, followed by incubation for 1 hour at 37° C. After two washes with PBS/0.05% Tween20, 100 µl of rabbit anti-swine IgG HRPO conjugate diluted 1:10.000 in PBS/1% BSA/0.5% Tween20 was added to the wells, and plates were incubated for 1 hour at 37° C. After three washes with PBS/0.05% Tween20, 100 µl/well of TMB "Super Slow"™ substrate was added to each well followed by incubation at room temperature for 10 min in the dark. Reactions were stopped by adding 100 µl of 25% sulfuric acid per well. The optical density (OD) at 450 nm was measured with an ELISA reader. Sera from naturally PEDV infected pigs were included as positive controls.

4.4. Results and Conclusions

Results are presented in Tables 4-6 below.

Piglets born from pregnant sows in groups 2 and 3 that were vaccinated with the method of vaccination according to the invention had significantly reduced percent mortality compared to piglets born from non-vaccinated sows (group 4), and compared to the group receiving the homologous prime-boost RP vaccine (group 1).

Sows primed orally with the heterologous method of vaccination (groups 2 and 3) had significantly higher PEDV-specific antibody levels in serum compared to sows vaccinated with the homologous prime-boost RP vaccine (group 1) and non-vaccinated control sows (group 4).

Piglets born from sows of groups 2 and 3 had significantly higher PEDV-specific neutralizing MDA compared to piglets born from sows of groups 1 and 4. The IgA antibody levels in piglets from sows of group 2 were significantly higher than in all other vaccinated groups.

TABLE 4

Piglet morbidity, mortality and weight gain demonstrated by litter

| Treatment | SowID | Number of Piglets | Number of Morbid Piglets | Number of Dead Piglets | Number of Morbid Piglets | Number of Dead Piglets | Average weight gain (lb.) from piglets that survived |
|---|---|---|---|---|---|---|---|
| 1 | 723 | 7 | 0 | 7 | 11 (37%) | 26 (87%) | 2.4 |
| (PED-RP) | 724 | 10 | 1 | 7 | | | |
| | 725 | 6 | 4 | 6 | | | |
| | 726 | 7 | 6 | 6 | | | |
| 2 | 715 | 10 | 4 | 10 | 4 (14%) | 11 (38%) | 3.8 |
| (Gantrez) | 716 | 5 | 0 | 1 | | | |
| | 717 | 9 | 0 | 0 | | | |
| | 718 | 5 | 0 | 0 | | | |

TABLE 4-continued

Piglet morbidity, mortality and weight gain demonstrated by litter

| Treatment | SowID | Number of Piglets | Number of Morbid Piglets | Number of Dead Piglets | Number of Morbid Piglets | Number of Dead Piglets | Average weight gain (lb.) from piglets that survived |
|---|---|---|---|---|---|---|---|
| 3 (PVP) | 719 | 7 | 0 | 6 | 2 (6%) | 16 (48%) | 5.7 |
|  | 720 | 10 | 2 | 7 |  |  |  |
|  | 721 | 9 | 0 | 0 |  |  |  |
|  | 722 | 7 | 0 | 3 |  |  |  |
| 4 (Control) | 727 | 7 | 0 | 7 | 12 (63%) | 19 (100%) | NA |
|  | 728 | 12 | 12 | 12 |  |  |  |

TABLE 5

PEDV-specific antibody response by FFN and IgA ELISA following vaccination in sows

| Treatment | Serum Mean Ln(FFN) | Serum Mean IgA ELISA |
|---|---|---|
| 1 (PEDV-RP) | 5.25 | 0.0685 |
| 2 (Gantrez) | 6.81 | 0.2135 |
| 3 (PVP) | 7.08 | 0.2830 |
| 4 (Control) | 2.30 | 0.0030 |

TABLE 6

PEDV-specific maternally derived antibodies in piglets prior to challenge

| Treatment | SowID | Number of Piglets | Ln(FFN) Average | IgA ELISA Average |
|---|---|---|---|---|
| 1 (PEDV-RP) | 723 | 7 | 4.54 | 0.0283 |
|  | 724 | 10 |  |  |
|  | 725 | 6 |  |  |
|  | 726 | 7 |  |  |
| 2 (Gantrez) | 715 | 10 | 6.27 | 0.2954 |
|  | 716 | 5 |  |  |
|  | 717 | 9 |  |  |
|  | 718 | 5 |  |  |
| 2 (PVP) | 719 | 7 | 6.28 | 0.3093 |
|  | 720 | 10 |  |  |
|  | 721 | 9 |  |  |
|  | 722 | 7 |  |  |
| 5 (Control) | 727 | 7 | 2.34 | 0.0384 |
|  | 728 | 12 |  |  |

LEGEND TO THE FIGURES

FIG. 1

PRRSV viremia results of the groups tested in the experiment of Example 1.

FIG. 2

Results of PRRSV viremia determinations from the experiments described in Example 2, as qPCR scores per group.

FIG. 3

Results of PRRSV viremia determinations from the experiments described in Example 3, as qPCR scores per group.

The invention claimed is:

1. A method of vaccination for protecting a target animal against infection or disease caused by a virus, wherein the method comprises
    administering a vaccine comprising a live attenuated form of said virus to the target animal, followed by
    administering a vaccine comprising a replicon particle (RP) encoding one or more antigens from said virus to the target animal.

2. The method of claim 1, wherein the target animal is a porcine.

3. The method of claim 2, wherein said virus is selected from the group consisting of a porcine epidemic diarrhoea virus (PEDV) and a porcine reproductive and respiratory syndrome virus (PRRSV).

4. The method of claim 1, wherein the vaccine comprising the RP comprises at least one further RP encoding one or more antigens from said virus.

5. The method of claim 1, wherein at least one viral antigen encoded by the RP is from a virus that is a variant within the species of the live attenuated virus.

6. The method of claim 1, wherein one or both of the vaccines comprise an adjuvant.

* * * * *